United States Patent
Wiesenfeldt et al.

(10) Patent No.: US 11,332,416 B2
(45) Date of Patent: May 17, 2022

(54) PROCESS FOR SYNTHESIZING FLUORINATED CYCLIC ALIPHATIC COMPOUNDS

(71) Applicant: WESTFÄLISCHE WILHELMS-UNIVERSITÄT MÜNSTER, Münster (DE)

(72) Inventors: Mario Patrick Wiesenfeldt, Münster (DE); Frank Glorius, Münster (DE); Zackaria Nairoukh, Münster (DE)

(73) Assignee: WESTFÄLISCHE WILHELMS-UNIVERSITÄT MÜNSTER, Münster (DE)

( * ) Notice: Subject to any disclaimer, the term of this patent is extended or adjusted under 35 U.S.C. 154(b) by 0 days.

(21) Appl. No.: 16/498,372

(22) PCT Filed: Feb. 23, 2018

(86) PCT No.: PCT/EP2018/054554
§ 371 (c)(1),
(2) Date: Sep. 26, 2019

(87) PCT Pub. No.: WO2018/177661
PCT Pub. Date: Oct. 4, 2018

(65) Prior Publication Data
US 2021/0261478 A1   Aug. 26, 2021

(30) Foreign Application Priority Data

Mar. 27, 2017 (DE) .......................... 102017106467.2

(51) Int. Cl.
| | | |
|---|---|---|
| C07B 35/02 | (2006.01) | |
| B01J 31/22 | (2006.01) | |
| C07C 17/354 | (2006.01) | |
| C07C 41/20 | (2006.01) | |
| C07C 67/303 | (2006.01) | |
| C07C 269/06 | (2006.01) | |
| C07D 209/08 | (2006.01) | |
| C07D 211/76 | (2006.01) | |
| C07D 307/79 | (2006.01) | |
| C07F 5/02 | (2006.01) | |
| C07F 7/18 | (2006.01) | |
| C07J 1/00 | (2006.01) | |

(52) U.S. Cl.
CPC ........... *C07B 35/02* (2013.01); *B01J 31/2273* (2013.01); *B01J 31/2295* (2013.01); *C07C 17/354* (2013.01); *C07C 41/20* (2013.01); *C07C 67/303* (2013.01); *C07C 269/06* (2013.01); *C07D 209/08* (2013.01); *C07D 211/76* (2013.01); *C07D 307/79* (2013.01); *C07F 5/027* (2013.01); *C07F 7/1892* (2013.01); *C07J 1/0059* (2013.01); *B01J 2231/646* (2013.01); *B01J 2531/822* (2013.01); *C07C 2601/14* (2017.05); *C07C 2601/16* (2017.05); *C07C 2602/10* (2017.05); *C07C 2602/28* (2017.05)

(58) Field of Classification Search
None
See application file for complete search history.

(56) References Cited

PUBLICATIONS

Wiesenfeldt et al. "Hydrogenation of fluoroarenes: Direct access to all-cis-(multi)fluorinated cycloalkanes" Science, 2017, vol. 357, No. 6354, pp. 908-912.*
Written Opinion of the International Searching Authority for PCT/EP2018/054554.
Stanger K et al "Hydrodefluorination of fluorobenzene catalyzed by rhodium metal prepared from [Rh(COD)2]+BF4- and supported on SiO2 and Pd—SiO2". Journal of Molecular Catalysis A:Chemical 207. 2004. pp. 59-68. Elsevier.
De Oliveira P R et al. "1,3-Diaxial steric effects and intramolecular hydrogen bonding in the conformational equilibria of new cis-1 ,3-disubstituted cyclohexanes using low temperature NMR spectra and theoretical calculations". Spectrochimica acta. part A: Molecular and Biomolecular Spectroscopy, Elsevier, vol. 62, No. 1-3, Nov. 1, 2005. pp. 30-37.
Hong Yang et al. "Hydrodefluorination of Fluorobenzene and 1,2-Difluorobenzene under Mild Conditions over Rhodium Pyridylphosphine and Bipyridyl Complexes Tethered on a Silica-Supported Palladium Catalyst", Organometallics, vol. 18, No. 12, Jun. 1, 1999 pp. 2285-2287.
Fache F et al."A Catalytic Stereo-and Chemo-Selective Method for the Reduction of Substituted Aromatics", Tetrahedron Letters, Elsevier,vol. 36, No. 6, Feb. 6, 1995, pp. 885-888.
Allen D P et al., "Rhodium N-heterocyclic carbene complexes: Synthesis, structure, NMR studies and catalytic activity",Journal of Organometallic Chemistry, Elsevier-Sequoia SA vol. 690, No. 24-25, Dec. 1, 2005, pp. 5736-5746.
Wolfgang A Herrmann et al. "Synthesis and Characterization of N-Heterocyclic Carbene Substituted Phosphine and Phosphite Rhodium Complexes and their Catalytic Properties in Hydrogenation Reactions", Advanced Synthesis & Catal, Wiley-VCH Verlag Gmbh, DE, vol. 349, No. 10, Jul. 2, 2007. pp. 1677-1691.
Yu Wei et al., "Highly Selective Hydrogenation of Aromatic Ketones and Phenols Enabled by Cyclic (Amino) (alkyl) carbene Rhodium Complexes", Journal of the American Chemical Society, vol. 137, No. 29, Jul. 29, 2015, pp. 9250-9253.

* cited by examiner

*Primary Examiner* — Joseph R Kosack
(74) *Attorney, Agent, or Firm* — Patent Technologies, LLC; Robert D. Gunderman, Jr.

(57) ABSTRACT

The present invention relates to a novel method for producing fluorinated cycloaliphatic compounds from the analogous aromatic compounds by hydrogenation with an Rh-carbene catalyst system.

9 Claims, No Drawings

PROCESS FOR SYNTHESIZING FLUORINATED CYCLIC ALIPHATIC COMPOUNDS

The present invention relates to the field of fluorinated cycloaliphatic compounds. Such compounds have an important role in the pharmaceutical or agrochemistry sectors on account of the polarity of the C—F bond with simultaneous steric similarity to C—H bonds and other effects. Furthermore, additive dipole effects with several identically oriented C—F bonds are interesting for materials chemistry applications.

Despite the importance of these compounds, effective production methods are not always given, such that there is a constant need for synthesis methods of fluorinated cycloaliphatic compounds.

An object is thus the provision of novel methods for producing such compounds. This object is achieved by a method according to Claim 1. Accordingly, a method for producing fluorinated cycloaliphatic compounds is provided, comprising the step of hydrogenation of an aromatic fluorine-containing precursor substance with a catalyst, comprising at least one rhodium atom and also at least one N-heterocyclic carbene ligand, in the presence of a reducing agent.

Surprisingly, it has become apparent that the corresponding fluorine-containing cycloaliphatic compounds can be obtained in this way, often with an outstanding yield, and F—H exchange, as would be expected in many analogous hydrogenations, either does not occur at all or only occurs to the extent that the fluorine-containing product can still be obtained in an acceptable yield in spite of this.

Surprisingly, in this case, in many applications, a whole range of functional groups are tolerated such as e.g. ester groups or protected amine/hydroxyl groups.

It has furthermore become apparent, surprisingly, that in the case in which the starting substance contains two or more fluorine atoms, the cis product is preferentially formed in many applications, which enables sterically defined products to be accessed.

The term "aromatic fluorine-containing substance" is especially intended to mean fluorinated substituted benzene derivatives, fluorinated carbocyclic or heterocyclic 5- or 6-membered rings with π electron sextet, and also fluorinated annellated aromatic polycycles.

It is pointed out that the term "aromatic fluorine-containing substance" is especially intended to mean that at least one fluorine is present as substituent on an aromatic ring.

Particular preference is given to aromatic fluorine-containing precursor substances which contain no heteroaromatic rings.

Alternatively, preference is given to aromatic fluorine-containing precursor substances which contain one or more benzanellated heteroaromatic rings.

The term "hydrogenation" is especially intended to mean that in total two hydrogens are added to a "double bond" of the aromatic compound. The present invention is not however restricted to hydrogen as specific reducing agent, even if this (as described below) is a preferred embodiment of the invention.

The term "N-heterocyclic carbene ligand" is intended to mean electron-rich nucleophilic compounds of divalent carbon species with an electron sextet, such as e.g. pyrrolidinylidenes, pyrrolidenes, imidazolylidenes, imidazolidinylidenes, piperidinylenes, hexahydropyrimidinylenes and triazolylidenes. Particular preference is given in this case to pyrrolidinylidenes, pyrrolidenes, imidazolylidenes and imidazolidinylidenes, more preferably pyrrolidinylidenes.

For the case in which the N-heterocyclic carbene ligand comprises a pyrrolidinylidene compound, it is especially preferred that, in the a position both to the nitrogen and to the carbene, there is no hydrogen. This has proven to be particularly effective for the hydrogenation in most applications of the present invention, since in this way the activity of the catalyst is not lowered by enamine formation, etc.

According to a preferred embodiment, the catalyst is used neat.

However, according to alternative embodiments, it may also be advantageous to produce the catalyst in situ. Thus, according to a preferred embodiment of the invention, the inventive method comprises two steps:

a) in situ synthesis of the catalyst used in step b) from suitable precursors b) carrying out the hydrogenation as described above and below.

As suitable rhodium-containing precursor, mention may especially be made of the cyclooctadiene rhodium chloride dimer ([Rh(COD)Cl]$_2$).

Step a) is preferably carried out by a suitable salt of the N-heterocyclic carbene with a strong base, preferably selected from NaOtBu, LDA, KOtBu, NaH, KHMDS, LiHMDS, being reacted with a rhodium-containing precursor, for example [Rh(COD)Cl]$_2$, optionally at elevated temperature. Halides, pseudohalides such as oxygen-containing anions, especially triflates and weakly-coordinating anions such as tetrafluoroborate, hexafluoroantimonate or hexafluorophosphate, can serve as anions in this case. Preferred solvents in this case are hexane, diethyl ether or tetrahydrofuran.

In the event that a different solvent is used in step b) than in step a), the solvent is then optionally removed between the two steps.

According to a preferred embodiment of the invention, the catalyst comprises at least one N-heterocyclic carbene ligand of the following structure:

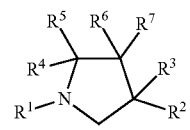

wherein $R^1$ to $R^5$, independently of one another, can be alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent CH$_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$— or —C≡C—, such that O and/or S atoms are not directly joined to one another, likewise optionally are replaced by aryl or heteroaryl preferably containing 1 to 30 C atoms (terminal CH$_3$ groups are understood, like CH$_2$ groups, in the sense of CH$_2$—H)

$R^6$ and $R^7$, independently of one another, can be hydrogen, alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent $CH_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal $CH_3$ groups are understood, like $CH_2$ groups, in the sense of $CH_2$—H)

and $R^1$ to $R^7$ can be substituted such that a ring optionally forms between $R^2$ and $R^3$, $R^4$ and $R^3$, $R^6$ and $R^7$, $R^1$ and $R^4/R^5$, $R^4/R^5$ and $R^6/R^7$ or $R^2/R^3$ and $R^6/R^7$.

General group definition: Within the description and the claims, general groups such as, e.g.: alkyl, alkoxy, aryl, etc., are claimed and described. Unless otherwise indicated, the following groups within the generally described groups are preferably used in the context of the present invention:

alkyl: linear and branched C1-C8 alkyls,
long-chain alkyls: linear and branched C5-C20 alkyls,
alkenyl: C2-C6 alkenyl,
cycloalkyl: C3-C8 cycloalkyl,
alkoxy: C1-C6 alkoxy,
long-chain alkoxy: linear and branched C5-C20 alkoxy
alkylene: selected from the group consisting of:
methylene; 1,1-ethylene; 1,2-ethylene; 1,1-propylidene; 1,2-propylene; 1,3-propylene; 2,2-propylidene; butan-2-ol-1,4-diyl; propan-2-ol-1,3-diyl; 1,4-butylene; cyclohexane-1,1-diyl; cyclohexane-1,2-diyl; cyclohexane-1,3-diyl; cyclohexane-1,4-diyl; cyclopentane-1,1-diyl; cyclopentane-1,2-diyl; and cyclopentane-1,3-diyl,
aryl; selected from aromatics having a molecular weight of less than 300 Da
arylene: selected from the group consisting of: 1,2-phenylene; 1,3-phenylene; 1,4-phenylene; 1,2-naphthalenylene; 1,3-naphthalenylene; 1,4-naphthalenylene; 2,3-naphthalenylene; 1-hydroxy-2,3-phenylene; 1-hydroxy-2,4-phenylene; 1-hydroxy-2,5-phenylene; and 1-hydroxy-2,6-phenylene,
heteroaryl; selected from the group consisting of: pyridinyl; pyrimidinyl; pyrazinyl; triazolyl; pyridazinyl; 1,3,5-triazinyl; quinoninyl; isoquinoninyl; quinoxalinyl; imidazolyl; pyrazolyl; benzimidazolyl; thiazolyl; oxazolidinyl; pyrrolyl; thiophenyl; benzothiophenyl, furyl, benzofuryl, carbazolyl; indolyl; and isoindolyl, wherein the heteroaryl can be bonded to the compound via any atom in the ring of the selected heteroaryl.
heteroarylene: selected from the group consisting of: pyridinediyl; quinolinediyl; pyrazodiyl; pyrazoldiyl; triazolediyl; pyrazinediyl, thiophenediyl; and imidazolediyl, wherein the heteroarylene functions as a bridge in the compound via any atom in the ring of the selected heteroaryl; special preference is given to: pyridine-2,3-diyl; pyridine-2,4-diyl; pyridine-2,5-diyl; pyridine-2,6-diyl; pyridine-3,4-diyl; pyridine-3,5-diyl; quinoline-2,3-diyl; quinoline-2,4-diyl; quinoline-2,8-diyl; isoquinoline-1,3-diyl; isoquinoline-1,4-diyl; pyrazole-1,3-diyl; pyrazole-3,5-diyl; triazole-3,5-diyl; triazole-1,3-diyl; pyrazine-2,5-diyl; and imidazole-2,4-diyl, thiophene-2,5-diyl, thiophene-3,5-diyl; a C1-C6 heterocycloalkyl, selected from the group consisting of: piperidinyl; piperidine; 1,4-piperazine, tetrahydrothiophene; tetrahydrofuran; 1,4,7-triazacyclononane; 1,4,8,11-tetraazacyclotetradecane; 1,4,7,10,13-pentaazacyclopentadecane; 1,4-diaza-7-thiacyclononane; 1,4-diaza-7-oxacyclononane; 1,4,7,10-tetraazacyclododecane; 1,4-dioxane; 1,4,7-trithiacyclononane; pyrrolidine; and tetrahydropyran, wherein the heteroaryl can be bonded to the C1-C6 alkyl via any atom in the ring of the selected heteroaryl.

heterocycloalkylene: selected from the group consisting of: piperidin-1,2-ylene; piperidin-2,6-ylene; piperidin-4,4-ylidene; 1,4-piperazin-1,4-ylene; 1,4-piperazin-2,3-ylene; 1,4-piperazin-2,5-ylene; 1,4-piperazin-2,6-ylene; 1,4-piperazin-1,2-ylene; 1,4-piperazin-1,3-ylene; 1,4-piperazin-1,4-ylene; tetrahydrothiophen-2,5-ylene; tetrahydrothiophen-3,4-ylene; tetrahydrothiophen-2,3-ylene; tetrahydrofuran-2,5-ylene; tetrahydrofuran-3,4-ylene; tetrahydrofuran-2,3-ylene; pyrrolidin-2,5-ylene; pyrrolidin-3,4-ylene; pyrrolidin-2,3-ylene; pyrrolidin-1,2-ylene; pyrrolidin-1,3-ylene; pyrrolidin-2,2-ylidene; 1,4,7-triazacyclonon-1,4-ylene; 1,4,7-triazacyclonon-2,3-ylene; 1,4,7-triazacyclonon-2,9-ylene; 1,4,7-triazacyclonon-3,8-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,5-ylene; 1,4,8,11-tetraazacyclotetradec-1,2-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-1,2-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4,7,10,13-pentaazacyclopentadec-2,3-ylene; 1,4,7,10,13-pentaazacyclopentadec-1,2-ylene; 1,4,7,10,13-pentaazacyclopentadec-2,2-ylidene; 1,4-diaza-7-thiacyclonon-1,4-ylene; 1,4-diaza-7-thiacyclonon-1,2-ylene; 1,4-diaza-7-thiacyclonon-2,3-ylene; 1,4-diaza-7-thiacyclonon-6,8-ylene; 1,4-diaza-7-thiacyclonon-2,2-ylidene; 1,4-diaza-7-oxacyclonon-1,4-ylene; 1,4-diaza-7-oxacyclonon-1,2-ylene; 1,4diaza-7-oxacyclonon-2,3-ylene; 1,4-diaza-7-oxacyclonon-6,8-ylene; 1,4-diaza-7-oxacyclonon-2,2-ylidene; 1,4-dioxan-2,3-ylene; 1,4-dioxan-2,6-ylene; 1,4-dioxan-2,2-ylidene; tetrahydropyran-2,3-ylene; tetrahydropyran-2,6-ylene; tetrahydropyran-2,5-ylene; tetrahydropyran-2,2-ylidene; 1,4,7-trithiacyclonon-2,3-ylene; 1,4,7-trithia-cyclonon-2,9-ylene; and 1,4,7-trithiacyclonon-2,2-ylidene, heterocycloalkyl: selected from the group consisting of: pyrrolinyl; pyrrolidinyl; morpholinyl; piperidinyl; piperazinyl; hexamethyleneimine; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thiacyclononanyl; 1,4-diaza-7-oxa-cyclononanyl; 1,4,7,10-tetraazacyclododecanyl; 1,4-dioxanyl; 1,4,7-trithiacyclononanyl; tetrahydropyranyl; and oxazolidinyl, wherein the heterocycloalkyl can be bonded to the compound via any atom in the ring of the selected heterocycloalkyl.

amine: the group —N(R)2, wherein each R is independently selected from: hydrogen; C1-C6 alkyl; C1-C6 alkyl-C6H5; and phenyl, wherein, if both R' are C1-C6 alkyl, both R' can form an —NC3 to NC5 heterocyclic ring, wherein the remaining alkyl chain forms an alkyl substituent on the heterocyclic ring halogen: selected from the group consisting of: F; Cl; Br and I, haloalkyl: selected from the group consisting of mono-, di-, tri-, poly- and perhalogenated linear and branched C1-C8 alkyl pseudohalogen: selected from the group consisting of —CN, —SCN, —OCN, N3, —CNO, —SeCN sulfonate: the group —S(O)2OR, wherein R is selected from: hydrogen; C1-C6 alkyl; phenyl; C1-C6 alkyl-C6H5; Li; Na; K; Cs; Mg; and Ca, sulfate: the group —OS(O)2OR, wherein R is selected from: hydrogen; C1-C6 alkyl; phenyl; C1-C6 alkyl-C6H5; Li; Na; K; Cs; Mg; and Ca, sulfone: the group —S(O)2R, wherein R is selected from: hydrogen; C1-C6 alkyl; phenyl; C1-C6 alkyl-C6H5 and amine (to give sulfonamide) selected from the group: —NR'2, wherein each R' is independently selected from: hydrogen; C1-C6 alkyl; C1C6 alkyl-C6H5; and phenyl, wherein, if both R" are C1-C6 alkyl, both R' can form an —NC3 to NC5 heterocyclic ring, wherein the remaining alkyl chain forms an alkyl substituent on the heterocyclic ring carboxylate: the group —C(O)OR, wherein R is selected from: hydrogen; C1-C6 alkyl; phenyl; C1-C6 alkyl-C6H5; Li; Na; K; Cs; Mg; and Ca, carbonyl: the group —C(O)R, wherein R is selected from: hydrogen; C1-C6 alkyl; phenyl; C1-C6 alkyl-C6H5 and amine (to give amide) selected from the group: —NR'2, wherein each R' is independently selected from: hydrogen; C1-C6 alkyl; C1C6 alkyl-C6H5; and phenyl, wherein, if both R' are C1-C6 alkyl, both R' can form an —NC3 to NC5 heterocyclic ring, wherein the remaining alkyl chain forms an alkyl substituent on the heterocyclic ring phosphonate: the group —P(O)(OR)2, wherein each R is independently selected from: hydrogen; C1-C6 alkyl; phenyl; C1-C6 alkyl-C6H5; Li; Na; K; Cs; Mg; and Ca, phosphate: the group —OP(O)(OR)2, wherein each R is independently selected from: hydrogen; C1-C6 alkyl; phenyl; C1-C6 alkyl-C6H5; Li; Na; K; Cs; Mg; and Ca, phosphine: the group —P(R)2, wherein each R is independently selected from: hydrogen; C1-C6-alkyl; phenyl; and C1-C6 alkyl-C6H5, phosphine oxide: the group —P(O)R2, wherein each R is independently selected from: hydrogen; C1-C6 alkyl; phenyl; and C1-C6 alkyl-C6H5 and amine (to give phosphonamidate) selected from the group: —NR'2, wherein each R' is independently selected from: hydrogen; C1-C6 alkyl; C1-C6 alkyl-C6H5; and phenyl, wherein, if both R' are C1-C6 alkyl, both R' can form an —NC3 to NC5 heterocyclic ring, wherein the remaining alkyl chain forms an alkyl substituent on the heterocyclic ring.

polyether: selected from the group consisting of —(O—$CH_2$—CH(R))$_n$—OH and —(O—$CH_2$—CH(R))$_n$—H, wherein R is independently selected from: hydrogen, alkyl, aryl, halogen, and n is from 1 to 250 silylalkyl: the group —$SiR_3$, wherein each R is independently selected from: hydrogen; C1-C6 alkyl; phenyl; C1-C6 alkyl-C6H5 and amine (to give sulfonamide) selected from the group: —NR'2, wherein each R' is independently selected from: hydrogen; C1-C6 alkyl; C1C6 alkyl-C6H5; and phenyl, wherein, if both R' are C1-C6 alkyl, both R' can form an —NC3 to NC5 heterocyclic ring, wherein the remaining alkyl chain forms an alkyl substituent on the heterocyclic ring silylalkyloxy: the group —$OSiR_3$, wherein each R is independently selected from: hydrogen; C1-C6 alkyl; phenyl; C1-C6 alkyl-C6H5 and amine (to give sulfonamide) selected from the group: —NR'2, wherein each R' is independently selected from: hydrogen; C1-C6 alkyl; C1C6 alkyl-C6H5; and phenyl, wherein, if both R' are C1-C6 alkyl, both R' can form an —NC3 to NC5 heterocyclic ring, wherein the remaining alkyl chain forms an alkyl substituent on the heterocyclic ring Unless indicated otherwise, the following groups are more preferably groups within the general group definition:

alkyl: linear and branched C1-C6 alkyl, long-chain alkyls: linear and branched C5-C10 alkyl, preferably C6-C8 alkyls, alkenyl: C3-C6 alkenyl, cycloalkyl: C6-C8 cycloalkyl.

alkoxy: C1-C4 alkoxy, long-chain alkoxy: linear and branched C5-C10 alkoxy, preferably linear C6-C8 alkoxy alkylene: selected from the group consisting of: methylene; 1,2-ethylene; 1,3-propylene; butan-2-ol-1,4-diyl; 1,4-butylene; cyclohexane-1,1-diyl; cyclohexane-1,2-diyl; cyclohexane-1,4-diyl; cyclopentane-1,1-diyl; and cyclopentane-1,2-diyl, aryl: selected from the group consisting of: phenyl; biphenyl; naphthyl; anthracenyl; and phenanthrenyl, arylene: selected from the group consisting of: 1,2-phenylene; 1,3-phenylene; 1,4-phenylene; 1,2-naphthalenylene; 1,4-naphthalenylene; 2,3-naphthalenylene and 1-hydroxy-2,6-phenylene, heteroaryl: selected from the group consisting of:

pyridinyl; pyrimidinyl; quinoninyl; pyrazolyl; triazolyl; isoquinoninyl; imidazolyl; and oxazolidinyl, wherein the heteroaryl can be bonded to the compound via any atom in the ring of the selected heteroaryl, heteroarylene: selected from the group consisting of: pyridine-2,3-diyl; pyridine-2,4-diyl; pyridine-2,6-diyl; pyridine-3,5-diyl; quinoline-2,3-diyl; quinoline-2,4-diyl; isoquinoline-1,3-diyl; isoquinoline-1,4-diyl; pyrazole-3,5-diyl; and imidazole-2,4-diyl, heterocycloalkyl: selected from the group consisting of:

pyrrolidinyl; morpholinyl; piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and piperazinyl, wherein the heteroaryl can be bonded to the compound via any atom in the ring of the selected heteroaryl heterocycloalkylene: selected from the group consisting of:

piperidin-2,6-ylene; piperidin-4,4-ylidene; 1,4-piperazin-1,4-ylene; 1,4-piperazin-2,3-ylene; 1,4-piperazin-2,6-ylene; tetrahydrothiophen-2,5-ylene; tetrahydrothiophen-3,4-ylene; tetrahydrofuran-2,5-ylene; tetrahydrofuran-3,4-ylene; pyrrolidin-2,5-ylene; pyrrolidin-2,2-ylidene; 1,4,7-triazacyclonon-1,4-ylene; 1,4,7-triazacyclonon-2,3-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4-diaza-7-thiacyclonon-1,4 ylene; 1,4-diaza-7-thiacyclonon-2,3-ylene; 1,4-diaza-7-thiacyclonon-2,2-ylidene; 1,4-diaza-7-oxacyclonon-1,4-ylene; 1,4diaza-7-oxacyclonon-2,3-ylene; 1,4-diaza-7-oxacyclonon-2,2-ylidene; 1,4-dioxan-2,6-ylene; 1,4-dioxan-2,2-ylidene; tetrahydropyran-2,6-ylene; tetrahydropyran-2,5-ylene; and tetrahydropyran-2,2-ylidene, a —C1-C6 alkyl-heterocycloalkyl, wherein the heterocycloalkyl is selected from the group consisting of: piperidinyl; 1,4-piperazinyl; tetrahydrofuranyl; 1,4,7-triazacyclononanyl; 1,4,8,11-tetraazacyclotetradecanyl; 1,4,7,10, 13-pentaazacyclopentadecanyl; 1,4,7,10-tetraazacyclododecanyl; and pyrrolidinyl, wherein the heterocycloalkyl can be bonded to the compound via any atom in the ring of the selected heterocycloalkyl amine: the group —N(R)2, wherein each R is independently selected from: hydrogen; C1-C6 alkyl; and benzyl halogen: selected from the group consisting of: F and Cl, sulfonate: the group —S(O)2OR, wherein R is selected from: hydrogen; C1-C6 alkyl; Na; K; Mg; and Ca, sulfate: the group —OS(O)2OR, wherein R is selected from: hydrogen; C1-C6 alkyl; Na; K; Mg; and Ca, sulfone: the group —S(O)2R, wherein R is selected from: hydrogen; C1-C6 alkyl; benzyl and amines selected from the group: —NR'2, wherein each R' is independently selected from: hydrogen; C1-C6 alkyl; and benzyl carboxylate: the group —C(O)OR, wherein R is selected from hydrogen; Na; K; Mg; Ca; C1-C6-alkyl; and benzyl carbonyl: the group —C(O)R, wherein R is selected from: hydrogen; C1-C6 alkyl; benzyl and amines selected from the group: —NR'2, wherein each R' is independently selected from: hydrogen; C1-C6 alkyl; and benzyl phosphonate: the group —P(O)(OR)2, wherein each R is independently selected from: hydrogen; C1-C6 alkyl; benzyl; Na; K; Mg; and Ca, phosphate: the group —OP(O)(OR)2, wherein R is independently selected from: hydrogen; C1-C6 alkyl; benzyl; Na; K; Mg; and Ca, phosphine: the group —P(R)2, wherein each R is independently selected from: hydrogen; C1-C6 alkyl; and benzyl phosphine oxide: the group —P(O)R2, wherein each R is independently selected from: hydrogen; C1-C6 alkyl; benzyl and amines selected from the group: —NR'2, wherein each R' is independently selected from: hydrogen; C1-C6 alkyl; and benzyl.

polyether: selected from the group consisting of —(O—CH$_2$—CH(R))$_n$—OH and —(O—CH$_2$—CH(R))$_n$—H, wherein R is independently selected from: hydrogen, methyl, halogen and n is from 5 to 50, preferably 10 to 25.

M, M$_n$ (n is an integer): metals, wherein two metals M are selected independently from one another, unless otherwise indicated.

According to a preferred embodiment of the invention, the catalyst comprises at least one N-heterocyclic carbene ligand of the following structure:

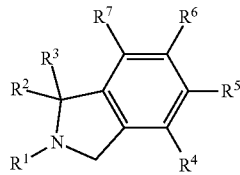

wherein $R^1$ to $R^3$, independently of one another, can be alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent CH$_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal CH$_3$ groups are understood, like CH$_2$ groups, in the sense of CH$_2$—H)

$R^4$ to $R^7$, independently of one another, can be hydrogen, alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent CH$_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal CH$_3$ groups are understood, like CH$_2$ groups, in the sense of CH$_2$—H)

and $R^1$ to $R^7$ can be substituted such that a ring optionally forms between $R^2$ and $R^3$, $R^1$ and $R^2/R^3$ or $R^2/R^3$ and $R^7$ or $R^6$ and $R^7$ or $R^5$ and $R^6$ or $R^4$ and $R^5$.

These two abovementioned N-heterocyclic carbene ligands are particularly preferred.

According to a preferred embodiment of the invention, the catalyst comprises at least one N-heterocyclic carbene ligand of the following structure:

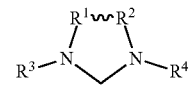

wherein $R^1$ or $R^2$ can either be a substituted or unsubstituted carbon or a nitrogen (wherein however $R^1$ and $R^2$ are not both nitrogen), wherein the substitutions are selected (independently of one another) from alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent CH$_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal CH$_3$ groups are understood, like CH$_2$ groups, in the sense of CH$_2$—H)

$R^3$ and $R^4$, independently of one another, can be alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent CH$_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal CH$_3$ groups are understood, like CH$_2$ groups, in the sense of CH$_2$—H)

wherein the bond between $R^1$ and $R^2$ can be a single or double bond and $R^1$ and $R^3$, on the one hand, and/or $R^2$ and $R^4$ on the other, can be substituted such that a ring forms between $R^1$ and $R^3$ or $R^2$ and $R^4$ According to a preferred embodiment, the catalyst comprises an N-heterocyclic carbene ligand of the following structure:

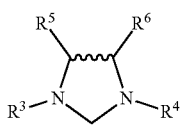

wherein $R^3$ and $R^4$ are as defined in the above catalyst, $R^5$ and $R^6$, independently of one another, can be hydrogen, alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent $CH_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal $CH_3$ groups are understood, like $CH_2$ groups, in the sense of $CH_2$—H)

and the bond between the ring carbons can be a single or double bond.

According to a preferred embodiment of the invention, the catalyst comprises at least one N-heterocyclic carbene ligand of the following structure:

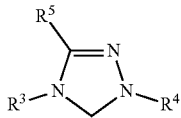

wherein $R^3$, $R^4$ and $R^5$ are as defined in the above catalyst.

According to a preferred embodiment of the invention, the catalyst comprises at least one N-heterocyclic carbene ligand of the following structure:

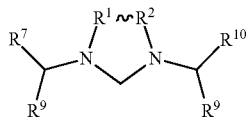

$R^1$ or $R^2$ can be either a substituted or unsubstituted carbon or a nitrogen (wherein however $R^1$ and $R^2$ are not both nitrogen), wherein the bond between $R^1$ and $R^2$ can be a single or double bond wherein $R^7$, $R^8$, $R^9$ and $R^{10}$, independently of one another, can be hydrogen, alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent $CH_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal $CH_3$ groups are understood, like $CH_2$ groups, in the sense of $CH_2$—H).

According to a preferred embodiment of the invention, the catalyst comprises at least one N-heterocyclic carbene ligand of the following structure:

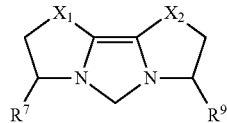

wherein $R^7$ and $R^9$ are as defined in the above catalyst and $X_1$ and $X_2$, independently of one another, can be O, NH or $CH_2$.

According to a preferred embodiment of the invention, the catalyst comprises, on the rhodium, at least one more further ligand, preference being given here to labile ligands. This is understood to include ligands, the bond of which to the rhodium is so weak that they are optionally, in the course of the reaction, at least temporarily no longer bonded to the rhodium.

Preferred labile ligands of this type are dialkenes, preferably COD, or norbornadienes, or alternatively to dialkenes, two ethylenes. Preferred possible ligands are cabonyl compounds, two chloride compounds, acetylacetonate, hydride ligands, halogen ligands, especially chloride, triflate, acetonitrile, weakly-coordinating anions such as tetrafluoroborate, or two phosphane compounds.

Preferably, the amount of catalyst before the start of the reaction is ≥0.001 mol % to ≤10 mol % (based on the aromatic precursor substance at the start of the reaction), more preferably ≥0.05 mol % to ≤5 mol %, even more preferably ≥0.1 mol % to ≤3 mol % and most preferably ≥0.2 mol % to ≤1 mol %. It has been found that even at these relatively small catalyst amounts, the reaction can nonetheless often be carried out with high yields.

Preferably, the method is carried out in an organic solvent, with the following having proven particularly suitable in practice (and hence being preferred): hexane, cyclohexane, dichloromethane, dichloroethane, dioxane, ethyl acetate, diethyl ether, THF, acetone, trifluoroethanol, or mixtures of these solvents. Hexane and cyclohexane are particularly preferred.

The method is preferably carried out at a temperature of ≥0° C. The upper limit is in principle only limited by the boiling point of the solvent used. Temperatures of ≥10° C. to ≤50° C. are more preferred, and room temperature, i.e. ≥20° C. to ≤30° C., is most preferred.

In the event that gaseous hydrogen is used as reducing agent, the preferred $H_2$ pressure (at the start of the reaction) is ≥3 bar, with particular preference given to ranges of ≥10 bar to ≤150 bar.

The reaction is preferably carried out for a reaction time of ≥3 h to ≤2 d, with particular preference given to reaction times of ≥5 h to ≤30 h.

The reaction is preferably carried out in the presence of a Lewis acid, preferably a Lewis acid which additionally has dehydrating properties. It has been found that in this way the yield can often be increased yet further. Preferred additives are selected from the group consisting of molecular sieve, preferably 4 Å molecular sieve or 3 Å molecular sieve, silica gel, $Al_2O_3$, aluminiumtriisopropylate, $TiO_2$, Florisil® or mixtures thereof.

The amount of Lewis acid is preferably from ≥70 to ≤600 mg, particularly preferably ≥150 to ≤450 mg per 1 mmol of reactant.

The abovementioned components and also the claimed components and components to be used according to the invention described in the exemplary embodiments are not subject to any particular exception conditions with regard to their size, shape, material selection and technical conception, and so the selection criteria known in the field of application can be applied without restriction.

Further details, features and advantages of the subject matter of the invention arise from the dependent claims and also from the description below of the accompanying examples in which—by way of example—multiple exemplary embodiments of the present invention are illustrated.

General Procedure I:

An oven-dried 9 ml screwtop glass jar filled with a stirrer bar and activated 4 Å molecular sieve (100 mg) was cooled under vacuum and filled with catalyst (0.1 to 1.5 mol %) and optionally solid reactant (1.0 mmol)—if the reactant used is solid—in the open air. The atmosphere in the glass jar was exchanged with argon (3×). After adding hexane (2 ml) and subsequently optionally liquid reactant (1.0 mmol)—if the reactant used is liquid—the screwtop glass jar was transferred under argon into a 150 ml steel autoclave under argon atmosphere, with the autoclave lid being open during the transfer and the autoclave being maintained under protective gas by means of a hose with argon flowing through it. The atmosphere in the autoclave was exchanged with hydrogen gas (3×), before 50 bar hydrogen pressure was added and the mixture was stirred for 24 h at 25° C. in a metal block (the temperature stated is the temperature of the metal block). After carefully releasing the pressure, the mixture was filtered over Whatman Filter©, washing being carried out with acetone (4×1 ml). The solvent was removed on a rotary evaporator at 45° C. and 500 mbar and the crude product was purified by column chromatography (silica gel, pentane/diethyl ether or dichloromethane/acetone depending on the polarity), the solvent subsequently being carefully removed on a rotary evaporator. Drying under high vacuum was not undertaken, in light of the volatility of most of the products. Particularly volatile products were purified by distillation. The stated diastereoselectivities relate to the isolated products and were determined from the $^1H$ or $^{19}F$ NMR spectra.

Using the general procedure 1, the following fluorinated cycloaliphatic compounds were produced, wherein in each case the following catalyst was used ((2-(2,6-diisopropylphenyl)-3,3-dimethyl-2-azaspiro[4.5]decan-1-ylidene)(cyclooctadienyl)rhodium(I) chloride):

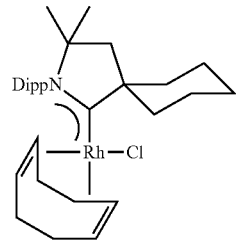

The results are summarized in the following table

| Example no. | Reactant | Product | Conditions and yield |
|---|---|---|---|
| 1 | Methyl 4-fluorobenzoate | Methyl cis-4-fluorocyclohexanecarboxylate | Catalyst loading: 0.5 mol % Colourless liquid; 80% yield, 9:1 dr |
| 2 | tert-butyl(2-fluorophenoxy)dimethylsilane | tert-butyl((cis-2-fluorocyclohexyl)oxy)dimethylsilane | Catalyst loading: 0.1 mol % Colourless liquid; 96% yield, 16:1 dr |
| 3 | 2-(4-fluorophenyl)-4,4,5,5-tetramethyl-1,3,2-dioxaborolane | 2-(cis-4-fluorocyclohexyl)-4,4,5,5-tetramethyl-1,3,2-dioxaborolane | Catalyst loading: 0.5 mol % Colourless liquid; 88% yield, 9:1 dr |

-continued

| Example no. | Reactant | Product | Conditions and yield |
|---|---|---|---|
| 4 | tert-butyl (4-fluorophenyl)carbamate | tert-butyl (cis-4-fluorocyclohexyl)carbamate | Catalyst loading: 0.5 mol % White solid; 81% yield, 6:1 dr |
| 5 | Fluorobenzene | Fluorocyclohexane | Catalyst loading: 0.1 mol % GC yield (product is known and is a colourless liquid) |
| 6 | 1,2,3-Trifluorobenzene | All-cis-1,2,3-trifluorocyclohexane | Catalyst loading: 0.1 mol % White solid; 81% yield, The product was filtered over silica gel (eluent: diethyl ether) and the solvent was distilled off using a Vigreux column. |
| 7 | 1,3,5-Trifluorobenzene | All-cis-1,3,5-trifluorocyclohexane | Catalyst loading: 0.1 mol % White solid; 65% yield, The product was filtered over silica gel (eluent: diethyl ether) and the solvent was distilled off using a Vigreux column. |
| 8 | 1,2,4,5-Tetrafluorobenzene | All-cis-1,2,4,5-tetrafluorocyclohexane | Catalyst loading: 0.5 mol % White solid; 60% yield, |
| 9 | Pentafluorobenzene | All-cis-1,2,3,4,5-pentafluorocyclohexane | Catalyst loading: 0.5 mol % White solid; 42% yield, |
| 10 | Hexafluorobenzene | All-cis-1,2,3,4,5,6-hexafluorocyclohexane | Catalyst loading: 0.5 mol % White solid; 22% yield, |

General Procedure II

A reaction vessel oven-dried at 135° C. (depending on the concentration, either a 9 ml screwtop glass jar (2.0 ml hexane, 0.5 M) or a 50 ml glass cylinder (15 ml hexane, 0.07 M)) filled with a magnetic stirrer bar and activated 4 Å molecular sieve or silica gel (150 mg or, with polyfluorinated aromatics, 450 mg of silica gel oven-dried at 135° C.) was cooled under vacuum and filled with catalyst (0.10 to 1.0 mol %) and optionally solid reactant (1.0 mmol)—if the reactant used is solid—in the open air. The atmosphere in the glass jar was exchanged with argon via a septum (3× vacuum/argon cycle). After adding hexane (2.0 ml or 15 ml) and subsequently optionally liquid reactant (1.0 mmol)—if the reactant used is liquid—the vessel was transferred under argon into a 150 ml steel autoclave under argon atmosphere, with the autoclave lid being open during the transfer and the autoclave being maintained under protective gas by means of a hose with argon flowing through it. The atmosphere in the autoclave was exchanged with hydrogen gas (3×10 bar hydrogen pressure/release cycle), before 50 bar hydrogen pressure was set and the mixture was stirred for 24 h at 25° C. in a metal block (the temperature stated is the temperature of the metal block). After carefully releasing the pressure, the mixture was purified by column chromatography (silica gel, pentane/diethyl ether or dichloromethane/acetone depending on the polarity), the solvent subsequently being carefully removed on a rotary evaporator. Drying under high vacuum was not undertaken, in light of the volatility of most of the products. Particularly volatile products were purified by distillation. The stated diastereoselectivities were determined by GC-MS, GC-FID or from the $^{19}$F NMR spectrum directly after the reaction. The notation >20:1 dr states that only a single diastereomer was detectable. Using the general procedure, the following fluorinated cycloaliphatic compounds were produced, wherein in each case the following catalyst was used ((2-(2,6-diisopropylphenyl)-3,3-dimethyl-2-azaspiro[4.5]decan-1-ylidene)(cyclooctadienyl)rhodium (I) chloride):

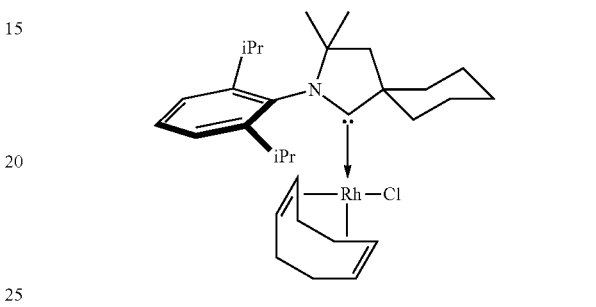

The results are summarized in the following table:

| Example no. | Reactant | Product | Conditions and yield |
|---|---|---|---|
| 1 | tert-Butyl(4-fluorphenoxy)dimethylsilane | tert-Butyl((cis-4-fluorocyclohexyl)oxy)dimethylsilane | Colourless oil<br>Catalyst loading: 0.10 mol %<br>Concentration: 0.5 M<br>93% yield, 13:1 dr<br>The reaction was also carried out on a larger scale;<br>5.0 mmol substrate<br>Catalyst loading: 0.10 mol %<br>Concentration: 0.5 M<br>400 mg molecular sieve<br>98% yield, 11:1 dr |
| 2 | tert-Butyl(2-fluorphenoxy)dimethylsilane | tert-Butyl((cis-2-fluorocyclohexyl)oxy)dimethylsilane | Colourless oil<br>Catalyst loading: 0.10 mol %<br>Concentration: 0.5 M<br>96% yield, 16:1 dr |
| 3 | 2-(4-Fluorophenyl)-4,4,5,5-tetramethyl-1,3,2-dioxaborolane | 2-(cis-4-Fluorocyclohexyl)-4,4,5,5-tetramethyl-1,3,2-dioxaborolane | Colourless oil<br>Catalyst loading: 0.50 mol %<br>Concentration: 0.5 M<br>88% yield, 9:1 dr |

-continued

| Example no. | Reactant | Product | Conditions and yield |
|---|---|---|---|
| 4 | 2-(3-Fluorophenyl)-4,4,5,5-tetramethyl-1,3,2-dioxaborolane | 2-(cis-3-Fluorocyclohexyl)-4,4,5,5-tetramethyl-1,3,2-dioxaborolane | Colourless oil<br>Catalyst loading: 0.50 mol %<br>Concentration: 0.5 M<br>82% yield, 8:1 dr |
| 5 | 2-(2-Fluorophenyl)-4,4,5,5-tetramethyl-1,3,2-dioxaborolane | 2-(cis-2-Fluorocyclohexyl)-4,4,5,5-tetramethyl-1,3,2-dioxaborolane | Colourless oil<br>Catalyst loading: 0.50 mol %<br>Concentration: 0.5 M<br>61% yield, >20:1 dr<br>The product decomposes slowly at room termperature. |
| 6 | tert-Butyl (4-fluorophenyl)carbamate | tert-Butyl (cis-4-fluorocyclohexyl)carbamate | White solid<br>Catalyst loading: 0.50 mol %<br>Concentration: 0.5 M<br>81% yield, 6:1 dr<br>The reaction was also carried out on a larger scale:<br>10 mmol substrate<br>Catalyst loading: 0.50 mol %<br>Concentration: 0.5 M in 7:1 hexane/dichloromethane<br>400 mg molecular sieve<br>47% yield, 7:1 dr |
| 7 | tert-Butyl (2-fluorophenyl)carbamate | tert-Butyl (cis-2-fluorocyclohexyl)carbamate | White solid<br>Catalyst loading: 0.50 mol %<br>Concentration: 0.5 M<br>63% yield, >20:1 dr |
| 8 | 4-Fluoroanisole | cis-1-fluoro-4-methoxycyclohexane | Colourless oil<br>Catalyst loading: 0.50 mol %<br>Concentration: 0.5 M<br>80% yield, 7:1 dr<br>After filtration over silica gel, the hexane was distilled off as azeotrope with acetone via a Vigreux column. |
| 9 | Methyl 4-fluorobenzoate | Methyl cis-4-fluorocyclohexanecarboxylate | Colourless oil<br>Catalyst loading: 0.50 mol %<br>Concentration: 0.5 M<br>80% yield, 9:1 dr |

| Example no. | Reactant | Product | Conditions and yield |
|---|---|---|---|
| 10 | tert-Butyl (4-fluorobenzyl)carbamate | tert-Butyl ((cis-4-fluorocyclohexyl)methyl)carbamate | Colourless oil<br>Catalyst loading: 0.50 mol %<br>Concentration: 0.5 M<br>90% $^{19}$F NMR yield (with hexafluorobenzene as internal standard), 7:1 dr.<br>The product was isolated together with traces of the reactant (approx. 7%). |
| 11 | 2-(2,4-Difluorophenyl)-4,4,5,5-tetramethyl-1,3,2-dioxaborolane | 2-(All-cis-2,4-difluorocyclohexyl)-4,4,5,5-tetramethyl-1,3,2-dioxaborolane | Colourless oil<br>Catalyst loading: 1.0 mol %<br>Concentration: 0.07 M<br>71% yield, 9:1 dr<br>The product decomposes slowly at room termperature. |
| 12 | tert-Butyldimethyl(3,4,5-trifluorophenoxy)silane | tert-Butyldimethyl((all-cis-3,4,5-trifluorocyclohexyl)oxy)silane | White solid<br>Catalyst loading: 1.0 mol %<br>Concentration: 0.07 M<br>68% yield, 7:1 dr |
| 13 | tert-Butyldimethyl(2,4,6-trifluorophenoxy)silane | tert-Butyldimethyl((all-cis-2,4,6-trifluorocyclohexyl)oxy)silane | Colourless oil<br>Catalyst loading: 1.0 mol %<br>Concentration: 0.07 M<br>97% yield, >20:1 dr |
| 14 | ((2-Fluoro-1,4-phenylene)bis(oxy))bis(tert-butyldimethylsilane) | ((All-cis-2-fluorocyclohexan-1,4-diyl)bis(oxy))bis(tert-butyldimethylsilane) | Colourless oil<br>Catalyst loading: 1.0 mol %<br>Concentration: 0.07 M<br>38% yield, >20:1 dr<br>The product was isolated together with traces of the defluorinated product (cis-1,4-bis((tert-butyldimethylsilyl)oxy)cyclohexane). |

| Example no. | Reactant | Product | Conditions and yield |
|---|---|---|---|
| 15 | ((Perfluoro-1,4-phenylene)bis(oxy))bis(tert-butyldimethylsilane) | ((All-cis-2,3,5,6-tetrafluorocyclohexane-1,4-diyl)bis(oxy))bis(tert-butyldimethylsilane) | White solid<br>Catalyst loading: 1.0 mol %<br>Concentration: 0.07 M<br>21% yield, >20:1 dr |
| 16 | Methyl 4-fluoro-2-hydroxybenzoate | Methyl 4-fluoro-2-hydroxycyclohex-1-ene-1-carboxylate | Yellowish oil<br>Catalyst loading: 1.0 mol %<br>Concentration: 0.07 M<br>42% yield<br>The stated enol was isolated together with traces (<5%) of the completely hydrogenated alcohol. |
| 17 | Fluorobenzene | Fluorocyclohexane | Catalyst loading: 0.10 mol %<br>Concentration: 0.5 M<br>90% GC-FID yield (with mesitylene as internal standard)<br>The product is known and is a colourless volatile liquid |
| 18 | 1,2-Difluorbenzene | cis-1,2-difluorocyclohexane | Catalyst loading: 0.10 mol %<br>Concentration 0.5 M<br>96% $^{19}$F NMR yield (with hexafluorobenzene as internal standard), 17:1 dr.<br>In a further experiment, the reaction was carried out in pentane. At the end of the reaction, the mixture was filtered over silica gel and the solvent was carefully removed. The readily volatile product was obtained with 72% yield and 17: dr and was contaminated with traces (approx. 1.0%) of fluorocyclohexane. |
| 19 | 1,2,3-Trifluorobenzene | All-cis-1,2,3-trifluorocyclohexane | Colourless oil<br>Catalyst loading: 0.10 mol %<br>Concentration: 0.5 M<br>81% yield, 6:1 dr<br>The reaction mixture was filtered over silica gel (eluent: diethyl ether) and the solvent was distileed off using a Vigreux column.<br>The reaction was also carried out on a larger scale:<br>25 mmol substrate<br>Catalyst loading: 0.10 mol %<br>Concentration: 1.0 M<br>400 mg molecular sieve<br>86% yield, 7:1 dr<br>After distilling off the solvent, the product was purified by distillation. |

| Example no. | Reactant | Product | Conditions and yield |
|---|---|---|---|
| 20 | 1,3,5-Trifluorobenzene | All-cis-1,3,5-trifluorocyclohexane | White solid<br>Catalyst loading: 0.10 mol %<br>Concentration: 0.5 M<br>65% yield (97% GC-FID yield with mesitylene as internal standard), >20:1 dr<br>The reaction mixture was filtered over silica gel (eluent: diethyl ether) and the solvent was distilled off using a Vigreux column. |
| 21 | 1,2,4,5-Tetrafluorbenzene | All-cis-1,2,4,5-tetrafluorocyclohexane | White solid<br>Catalyst loading: 0.50 mol %<br>Concentration: 0.07 M<br>60% yield, >20:1 dr |
| 22 | 1,2,3,4-Tetrafluorbenzene | All-cis-1,2,3,4-tetrafluorocyclohexane | White solid<br>Catalyst loading: 0.50 mol %<br>Concentration: 0.5 M<br>26% yield, >20:1 dr |
| 23 | Pentafluorobenzene | All-cis-1,2,3,4,5-pentafluorocyclohexane | White solid<br>Catalyst loading: 1.0 mol %<br>Concentration: 0.5 M<br>42% yield, >20:1 dr<br>The reaction was also carried out with 450 mg of silica gel oven-dried at 135° C., instead of molecular sieve.<br>(89% yield, >20:1 dr) |
| 24 | Hexafluorobenzene | All-cis-1,2,3,4,5,6-hexafluorocyclohexane | White solid<br>Catalyst loading: 0.50 mol %<br>Concentration: 0.07 M<br>34% yield, >20:1 dr<br>The reaction was also carried out with activated pulverulent molecular sieve (89% NMR yield).<br>The reaction was also carried out with 450 mg of silica gel oven-dried at 135° C., instead of molecular sieve.<br>(88% yield, >20:1 dr)<br>The reaction was also carried out on a 20 mmol scale (0.50 mol % catalyst loading, 35 ml hexane, 4.5 g silica gel, 62% yield). |
| 25 | Perfluoronaphthalene | All-cis-1,2,3,4,5,6,7,8-octafluoro-1,2,3,4-tetrahydronaphthalene | White solid<br>Catalyst loading: 0.50 mol %<br>Concentration: 0.14 M<br>56% yield, >20:1 dr |

-continued

| Example no. | Reactant | Product | Conditions and yield |
|---|---|---|---|
| 26 | Perfluoro-1,1′-biphenyl | 1,2,3,4,5-Pentafluoro-6-(all-cis-2,3,4,5,6-pentafluorocyclohexyl)benzene | White solid<br>Catalyst loading: 0.50 mol %<br>Concentration: 0.07 M<br>12% yield, >20:1 dr |
| 27 | 4,4′-Difluoro-1,1′-biphenyl | All-cis-4,4′-difluoro-1,1′-bi(cyclohexane) | White solid<br>Catalyst loading: 0.50 mol %<br>Concentration: 0.5 M<br>96% yield, 15:1 dr<br>The compound was obtained as a 7:1 mixture of two stable conformers. |
| 28 | 1-Fluoronaphthalene | All-cis-1-fluorodecahydronaphthalene | Colourless oil<br>Catalyst loading: 1.0 mol %<br>Concentration: 0.5 M<br>74% yield, 6:1 dr |
| 29 | 2-Fluoro-1,1′-biphenyl | cis-2-fluoro-1,1′-bis(cyclohexane) | Colourless oil<br>Catalyst loading: 0.50 mol %<br>Concentration: 0.5 M<br>91% yield, 20:1 dr |
| 30 | tert-butyl 6-fluoro-1H-indole-1-carboxylate | tert-butyl all-cis-6-fluorooctahydro-1H-indole-1-carboxylate | Colourless oil<br>Catalyst loading: 1.0 mol %<br>Concentration: 0.07 M<br>83% yield, 1.5:1 dr |
| 31 | tert-butyl 5-fluoro-1H-indole-1-carboxylate | tert-butyl all-cis-5-fluorooctahydro-1H-indole-1-carboxylate | Colourless oil<br>Catalyst loading: 1.0 mol %<br>Concentration: 0.07 M<br>52% yield, 6:1 dr<br>Silica gel (150 mg) oven-dried at 135° C. was used instead of molecular sieve. |

| Example no. | Reactant | Product | Conditions and yield |
| --- | --- | --- | --- |
| 32 | 5-Fluorobenzofuran | All-cis-5-fluorooctahydrobenzofuran | Colourless oil<br>Catalyst loading: 1.0 mol %<br>Concentration: 0.07 M<br>85% yield, 8:1 dr |
| 33 | 3-Fluoropyridin-2(1H)-one | 3-Fluoropiperidin-2-one | White solid<br>Catalyst loading: 1.0 mol %<br>Concentration: 0.07 M<br>53% yield<br>Silica gel (150 mg) oven-dried at 135° C. was used instead of molecular sieve. |
| 34 | 3-Deoxy-3-fluoroestrone | 3-Deoxy-3-fluoro-all-cis-hexahydroestrone | White solid<br>Catalyst loading: 1.0 mol %<br>Concentration: 0.02 M<br>81% yield<br>The reaction was carried out with a batch size of 0.50 mmol of the substrate, using silica gel (150 mg) oven-dried at 135° C. The ratio of the main diastereomer to all other diasteromers is 3:1. |

In a further experiment, the hydrogenation of tert-butyl (4-fluorophenoxy)dimethylsilane using the cationic ((2-(2,6-diisopropylphenyl)-3,3-dimethyl-2-azaspiro[4.5]decan-1-ylidene)(cyclooctadienyl) rhodium(I)tetrafluorborate) complex (0.10 mmol substrate, catalyst loading: 5.0 mol %, 0.1 M in hexane) in the absence of molecular sieve or comparable additive, according to the general procedure, was tested. 71% GC yield of tert-butyl((cis-4-fluorocyclohexyl)oxy)dimethylsilane (17:1 dr) was observed.

The structural formula of the cationic complex is as follows:

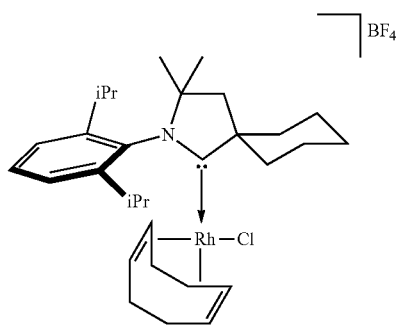

In a further experiment, the hydrogenation of tert-butyl (4-fluorophenoxy)dimethylsilane using the cationic 1-(2,6-diisopropylphenyl)-2,2,4,4-tetramethyl-3,4-dihydro-2H-pyrrol-1-ylidene(cyclooctadienyl) rhodium(I)chloride complex (0.10 mmol substrate, catalyst loading: 0.1 mol %, 0.05 M in hexane) in the presence of 4 Å molecular sieve (50 mg), according to the general procedure, was tested. 73% GC yield of tert-butyl((cis-4-fluorocyclohexyl)oxy)dimethylsilane (13:1 dr) was observed.

The structural formula of the complex used is as follows:

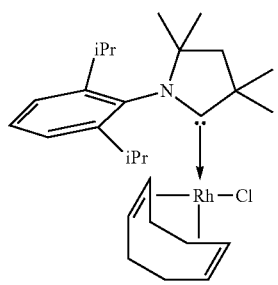

A further experiment was carried out with 1-(4-fluorophenyl)-2-phenylethan-1-one as reactant (0.10 mmol) and also trifluoroethanol as solvent (0.5 M) and 5.0 mol % of (R)-(2-(3,3-dimethylbutan-2-yl)-3,3-diphenylisoindolin-1-ylidene)(cyclooctadienyl) rhodium(I)chloride as catalyst; the structural formula is as follows:

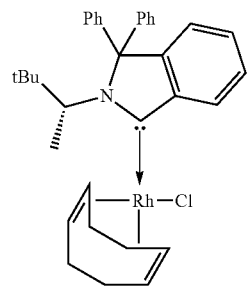

(A mixture of the two catalyst diastereomers was used). This gave 24% $^{19}$F NMR yield of 2-cyclohexyl-1-(4-fluorocyclohexyl)ethan-1-ol.

General Procedure III:

A 9 ml screwtop glass jar oven-dried at 135° C., filled with a magnetic stirrer bar and activated 4 Å molecular sieve or silica gel (250 mg) was cooled under vacuum and filled in the open air with catalyst (2.0 to 3.0 mol %) and nonvolatile reactant (0.5 mmol)—if the reactant used is nonvolatile. The atmosphere in the glass jar was exchanged with argon via a septum (3× vacuum/argon cycle). After adding the solvent (dichloromethane or mixtures of hexane and dichloromethane, 2.0 ml) and subsequently optionally volatile reactant (0.5 mmol)—if the reactant used is volatile—the vessel was transferred under argon into a 150 ml steel autoclave under argon atmosphere, with the autoclave lid being open during the transfer and the autoclave being maintained under protective gas by means of a hose with argon flowing through it. The atmosphere in the autoclave was exchanged with hydrogen gas (3×10 bar hydrogen pressure/release cycle), before 50 bar hydrogen pressure was set and the mixture was stirred for 24 h at 25° C. in a metal block (the temperature stated is the temperature of the metal block). After carefully releasing the pressure, the mixture was purified by column chromatography (silica gel, pentane/ethyl acetate depending on the polarity), the solvent subsequently being carefully removed on a rotary evaporator. Drying under high vacuum was not undertaken, in light of the volatility of most of the products. Particularly volatile products were purified by distillation. The stated diastereoselectivities were determined by GC MS directly after the reaction.

Using the general procedure, the following fluorinated cycloaliphatic compounds were produced, wherein in each case the following catalyst was used ((2-(2,6-diisopropylphenyl)-3,3-dimethyl-2-azaspiro[4.5]decan-1-ylidene)(cyclooctadienyl)rhodium(I) chloride):

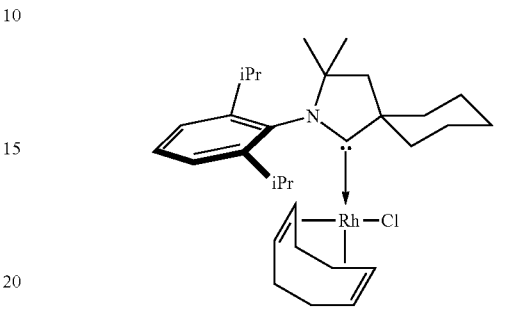

The results are summarized in the following table:

| Example no. | Reactant | Product | Conditions and yield |
|---|---|---|---|
| 1 | Triethoxy(3-fluorophenyl)silane | triethoxy(cis-3-fluorocyclohexyl)silane | Colourless oil<br>Catalyst loading: 3.00 mol %<br>72% yield, 8:1 dr<br>Solvent: CH$_2$Cl$_2$/hexane = 4:1 |
| 2 | (4-fluorophenyl)triethylsilane | (cis-4-fluorocyclohexyl)triethylsilane | Colourless oil<br>Catalyst loading: 2.00 mol %<br>Solvent: hexane.<br>66% yield, 6:1 dr |

The individual combinations of the constituents and the features of the abovementioned embodiments are exemplary: the exchange and substitution of this teaching with other teaching contained within this document with the cited documents are likewise expressly envisaged. Those skilled in the art are aware that variations, modifications and other embodiments described here may also arise without departing from the inventive concept and the scope of the invention.

Accordingly, the abovementioned description is to be considered as exemplary and nonlimiting. The word "comprise" used in the claims does not exclude other constituents or steps. The indeterminate article "a" does not exclude the meaning of a plural. The mere fact that specific measures are claimed in mutually different claims does not mean that a combination of these measures cannot be used advantageously. The scope of the invention is defined in the following claims and the associated equivalents.

The invention claimed is:

1. A method for producing fluorinated cycloaliphatic compounds comprising the step of hydrogenation of an aromatic fluorine-containing precursor substance with a catalyst, comprising at least one rhodium atom and also at least one N-heterocyclic carbene ligand, in the presence of a reducing agent.

2. The method according to claim 1, wherein the N-heterocyclic carbene ligand comprises a compound selected from the group consisting of pyrrolidinylidenes, pyrrolidenes, imidazolylidenes, imidazolidinylidenes, piperidinylenes, hexahydropyrimidinylenes and triazolylidenes.

3. The method according to claim 1, wherein the N-heterocyclic carbene ligand comprises a pyrrolidinylidene compound in which, in the u position both to the nitrogen and to the carbene, there is no hydrogen.

4. The method according to claim 1, wherein the N-heterocyclic carbene ligand comprises one of the following compounds:

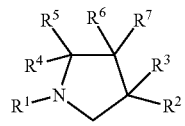

wherein
$R^1$ to $R^5$, independently of one another, can be alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent $CH_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal $CH_3$ groups are understood, like $CH_2$ groups, in the sense of $CH_2$—H)
$R^6$ and $R^7$, independently of one another, can be hydrogen, alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent $CH_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal $CH_3$ groups are understood, like $CH_2$ groups, in the sense of $CH_2$—H)
and $R^1$ to $R^7$ can be substituted such that a ring optionally forms between $R^2$ and $R^3$, $R^4$ and $R^3$, $R^6$ and $R^7$, $R^1$ and $R^4/R^5$, $R^4/R^5$ and $R^6/R^7$ or $R^2/R^3$ and $R^6/R^7$;

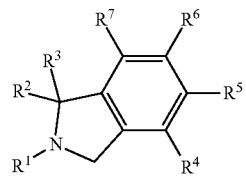

wherein
$R^1$ to $R^3$, independently of one another, can be alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent $CH_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal $CH_3$ groups are understood, like $CH_2$ groups, in the sense of $CH_2$—H)
$R^4$ to $R^7$, independently of one another, can be hydrogen, alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent $CH_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal $CH_3$ groups are understood, like $CH_2$ groups, in the sense of $CH_2$—H)
and $R^1$ to $R^7$ can be substituted such that a ring optionally forms between $R^2$ and $R^3$, $R^1$ and $R^2/R^3$ or $R^2/R^3$ and $R^7$ or $R^6$ and $R^7$ or $R^5$ and $R^6$ or $R^4$ and $R^5$;

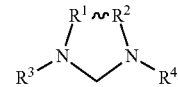

wherein
$R^1$ or $R^2$ can either be a substituted or unsubstituted carbon or a nitrogen (wherein however $R^1$ and $R^2$ are not both nitrogen), wherein the substitutions are selected (independently of one another) from alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent $CH_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal $CH_3$ groups are understood, like $CH_2$ groups, in the sense of $CH_2$—H)
$R^3$ and $R^4$, independently of one another, can be alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent $CH_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal $CH_3$ groups are understood, like $CH_2$ groups, in the sense of $CH_2$—H)

wherein the bond between $R^1$ and $R^2$ can be a single or double bond and $R^1$ and $R^3$, on the one hand, and/or $R^2$ and $R^4$ on the other, can be substituted such that a ring forms between $R^1$ and $R^3$ or $R^2$ and $R^4$

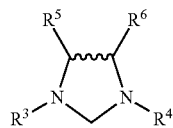

wherein $R^3$ and $R^4$ are as defined in the above catalyst, $R^5$ and $12^6$, independently of one another, can be hydrogen, alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent $CH_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal $CH_3$ groups are understood, like $CH_2$ groups, in the sense of $CH_2$—H)

and the bond between the ring carbons can be a single or double bond;

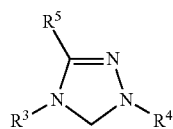

wherein $R^3$, $R^4$ and $R^5$ are as defined in the above catalyst,

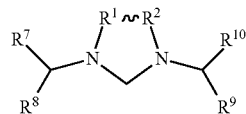

wherein $R^1$ or $R^2$ can be either a substituted or unsubstituted carbon or a nitrogen (wherein however $R^1$ and $R^2$ are not both nitrogen), wherein the bond between $R^1$ and $R^2$ can be a single or double bond, wherein $R^7$, $R^8$, $R^9$ and $R^{10}$, independently of one another, can be hydrogen, alkyl, long-chain alkyl, alkoxy, long-chain alkoxy, cycloalkyl, haloalkyl, aryl, haloaryl, heteroaryl, heterocycloalkylene, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, silylalkyl, silylalkyloxy, wherein, in suitable radicals, one or more non-adjacent $CH_2$ groups can be independently replaced by —O—, —S—, —NH—, —NR°—, —SiR°R°°—, —CO—, —COO—, —OCO—, —OCO—O—, —SO$_2$—, —S—CO—, —CO—S—, —CY$^1$=CY$^2$ or —C≡C—, such that O and/or S atoms are not directly joined to one another, likewise optionally are replaced by aryl or heteroaryl preferably containing 1 to 30 C atoms (terminal $CH_3$ groups are understood, like $CH_2$ groups, in the sense of $CH_2$—H);

and also

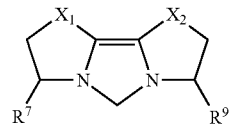

wherein $R^7$ and $R^9$ are as defined in the above catalyst and $X_1$ and $X_2$, independently of one another, can be O, NH or $CH_2$.

5. The method according to claim 1, wherein the amount of the catalyst is initially ≥0.05 mol % to ≤5 mol % (based on the aromatic precursor substance at the start of the reaction).

6. The method according to claim 1, wherein the method is carried out in an organic solvent.

7. The method according to claim 1, wherein the method is carried out at a temperature of ≥0° C.

8. The method according to claim 1, wherein the method is carried out using gaseous hydrogen as reducing agent and the $H_2$ pressure (at the start of the reaction) is ≥10 bar.

9. The method according to claim 1, wherein the reaction time is ≥4 h to ≤2 d.

* * * * *